(12) United States Patent
Anthony

(10) Patent No.: US 8,795,643 B1
(45) Date of Patent: Aug. 5, 2014

(54) METHOD OF PREPARING A HAIR TREATMENT FORMULATION COMPRISING NANOPARTICLES IN SOLUTION AND METHOD OF HAIR TREATMENT UTILIZING A TREATMENT FORMULATION COMPRISING NANOPARTICLES IN SOLUTION

(76) Inventor: Michael Mark Anthony, Lakeworth, FL (US)

( * ) Notice: Subject to any disclaimer, the term of this patent is extended or adjusted under 35 U.S.C. 154(b) by 14 days.

(21) Appl. No.: 13/218,894

(22) Filed: Aug. 26, 2011

Related U.S. Application Data

(60) Provisional application No. 61/518,114, filed on Apr. 29, 2011.

(51) Int. Cl.
*A61Q 5/12* (2006.01)
*A61Q 5/00* (2006.01)

(52) U.S. Cl.
USPC ............... 424/70.14; 424/70.11; 424/70.51

(58) Field of Classification Search
None
See application file for complete search history.

(56) References Cited

U.S. PATENT DOCUMENTS

| | | | |
|---|---|---|---|
| 2,389,771 A | 11/1945 | Gaver | |
| 2004/0010864 A1* | 1/2004 | Vic et al. | 8/405 |
| 2010/0172943 A1* | 7/2010 | Edelson et al. | 424/401 |

FOREIGN PATENT DOCUMENTS

| | | | |
|---|---|---|---|
| WO | WO 2009/012303 | * | 1/2009 |

OTHER PUBLICATIONS

Simi, et al.; Hydrophobic Grafted and Cross-Linked Starch Nanoparticles for Drug Delivery; Bioprocess Biosyst Eng (2007) 30:173-180.
Lemarchand, et al.; Novel Polyester-Polysaccharide Nanoparticles; Pharmaceutical Research, vol. 20, No. 8, Aug. 2003: 1284-1292.
Hornig, et al.; Synthesis and Characterization of Sulfur Containing Dextran- and $\beta$-Cyclodextrin Derivatives; Polymer Bulletin 59, 65-71 (2007).
Rodrigues, et al.; Novel core(polyester)-shell(polysaccharide) Nanoparticles: Protein Loading and Surface Modification with . . . ; Journal of Controlled Release 92 (2003):103-112.
Wang, et al.; Exchange of (3 mercaptopropyl) trimethoxysilane with alkanethiol and co-adsorption on silver powder; vol. 287, Issues 1-3 Sep. 15, 2006 (abstract only).
Euro Nano Forum 2009 Conclusions; Nanotechnology for Sustainable Economy; Jun. 2-5, 2009 ; Prague (Czech Republic).
Khan, et al.; Rheology of Protein Gels Synthesized through a Combined Enzymatic and Heat Treatment method; Int Journal of Biological Macromolecules, 31 (2002) 37-44.
Franco Bellesia et al.; Volatile Compounds in Food Aroma: Biosynthesis and Biotransformations; Progress in Biological Chirality; Chapter 20; 2004.
Yamaguchi, et al.; Preparation of Partially N-succinylated Chitosans and their Cross-Linked Gels; Carbohydrate Research, 88 (1981) 172-175.
Bodmeier, et al. Spherical Agglomerates of Water-Insoluble Drugs; Journal of Pharmaceutical Science, vol. 78, No. 11, Nov. 1989.

* cited by examiner

*Primary Examiner* — Jyothsna Venkat
(74) *Attorney, Agent, or Firm* — Malloy & Malloy, P.L.

(57) ABSTRACT

A hair treatment formulation comprises a plurality of composite nanoparticles in solution. The composite nanoparticles are specifically prepared having an inner core, comprising at least one protein, an intermediate starch-thiolate layer, and an outer layer comprising chitosan or modified chitosan. At least one treatment component is embedded in at least one of the inner core, intermediate layer, or outer layer. A method of preparing a hair treatment formulation comprising composite nanoparticles is disclosed along with a method of use of a hair treatment formulation comprising a plurality of composite nanoparticles.

21 Claims, 3 Drawing Sheets

FIGURE 1 – TABLE 1

| Component | Minimum Weight % | Maximum Weight % | Manufacturer/Supplier |
|---|---|---|---|
| Water | Balance to 100% | Balance to 100% | - - |
| Cyamopsis Tetragonoloba | 2.00 | 5.00 | Tic Gums Inc. |
| Isooctyl thioglycolic acid and thioglycolic acid | 2.00 | 5.00 | Evans Chemicals (Chemrex) |
| Perfume / Scent | 1.00 | 4.00 | Cosmo International |
| (3-mercaptopropyl)trimethoxysilane | 0.50 | 4.00 | Dow Corning Chemicals |
| Silicone oil | 0.50 | 4.00 | Parchem Trading LTD. |
| Hydrolyzed cysteine and lysine proteins | 0.50 | 2.00 | Dow Corning Chemicals |
| Citronella oil | 0.50 | 2.00 | Cosmo International |
| Chitosan or modified chitosan | 0.10 | 2.00 | Keratonics Inc. |
| Argan oil | 0.10 | 1.00 | Azelis Espana S.A. |
| Soy bean oil | 0.10 | 1.00 | Snowdrift Farms Inc. |
| Olive oil | 0.10 | 1.00 | Snowdrift Farms Inc. |
| Wheat germ oil | 0.10 | 1.00 | Snowdrift Farms Inc. |
| Acetyl Salicylic acid | 0.10 | 1.00 | Parchem Trading LTD. |
| Sorbitol | 0.10 | 1.00 | Parchem Trading LTD. |
| Erythritol | 0.10 | 1.00 | Parchem Trading LTD. |
| Starch | 0.10 | 1.00 | Parchem Trading LTD. |
| Salicylic acid | 0.10 | 1.00 | Parchem Trading LTD. |
| Oat straw powder | 0.10 | 1.00 | Parchem Trading LTD. |
| Glacial Acetic acid (99.9%) | 0.10 | 0.50 | Parchem Trading LTD. |
| Hydrogen peroxide | 0.10 | 0.50 | Univar Chemicals LLC |
| Agar-Agar gum | 0.10 | 0.50 | Snowdrift Farms Inc. |
| Pyroglutamic acid (PCA) | 0.10 | 0.50 | Snowdrift Farms Inc. |
| Caprylcyl hydrolyzed cysteine | 0.00 | 0.50 | Snowdrift Farms Inc. |
| Amp-isostearoyl hydrolyzed soy protein | 0.00 | 0.50 | Snowdrift Farms Inc. |
| Amp-isostearoyl gelatin/cysteine and amino acids lysine | 0.00 | 0.25 | Snowdrift Farms Inc. |
| Abies balsamea extract | 0.02 | 0.25 | Alpha Aeser Inc. |
| Sodium Hydroxide (50% solution) | 0.00 | 0.25 | Parchem Trading LTD. |
| Urea peroxide | 0.00 | 0.25 | Alpha Aeser Inc. |
| TOTAL | 100.00 | 100.00 | - - |

METHOD OF PREPARING A HAIR TREATMENT FORMULATION COMPRISING NANOPARTICLES IN SOLUTION AND METHOD OF HAIR TREATMENT UTILIZING A TREATMENT FORMULATION COMPRISING NANOPARTICLES IN SOLUTION

CLAIM OF PRIORITY

The present application is based on and a claim of priority is made under 35 U.S.C. Section 119(e) to a provisional patent application that is in the U.S. Patent and Trademark Office, namely, that having Ser. No. 61/518,114 and a filing date of Apr. 29, 2011, which is incorporated herein in its entirety by reference.

BACKGROUND OF THE INVENTION

1. Field of the Invention

The present invention includes a method of preparation of a hair treatment formulation comprising nanoparticles in solution which are specifically structured such that one or more preselected hair treatment components may be embedded therein. The nanoparticles are prepared having a range of pH values which, in conjunction with the pH values of the carrier solution itself, effect the opening and closing of the hair cuticles, and thus, the delivery and retention of the embedded hair treatment components therein. The present invention further comprises a method for treatment of a user's hair utilizing a solution of specifically structured nanoparticles having one or more treatment component embedded therein.

2. Description of the Related Art

Hair is made from proteins that have a special structure forming long extended fibers with very good mechanical properties. The hair shaft comprises an outer protective layer of layered scales known as the cuticle layer. This cuticle layer has tiny elongated scales that overlap to form a covering around the hair shaft and this covering can open to allow access into the inner areas of the hair shaft. The cuticle layer is hydrophobic and does not get saturated with water and other chemicals and it is made from cysteine, an amino acid found in many proteins in the body, that form very hard strong matrices that have very good mechanical properties. Below this outer cuticle layer of scales is a layer of the cuticle structure that is very rich in cysteine proteins called the exocuticle. This layer comprises about 37% of the total cysteine protein content of the cuticle layers.

Just below the cuticle layer is a column of cells called the cortex. The cortex is made up a rigid network of strong cells and is mechanically the most important structure that controls the tensile strength, flexure, and shape of hair fibers. These cells are large and elongated and are aligned along the axis of the hair shaft forming the rigid network. This rigid network of cells is primarily made from cysteine proteins and other amino acids held together by disulfide bonds. The disulfide bond is a covalent chemical bond binding two sulfur atoms together. As the hair grows, it builds structural meshes of covalently bound cysteine proteins forming the general fiber shape of the hair. The shape of the fiber is determined by the manner in which the network of disulfide bonds is formed along the hair shaft. Kinks and bends occur as the general shape that the hair shaft takes for minimal stress from the forces of the disulfide bonds. Modifying this cellular structure by weakening the covalent bonds and de-stressing the hair fiber is the main method that has been used to straighten hair in the past.

Many existing hair smoothing, straightening and conditioning cosmetic formulations use very harsh and environmentally unfriendly chemicals such as high concentrations of formaldehyde, glutaraldehyde, thioglycolic acids and other very unfriendly chemicals. The chemistry of these existing formulations depend upon breaking covalent disulfide bonds and/or charged ionic exchanges that bind conditioning agents to the hair cuticle.

In lye based systems, a strong base, such as sodium hydroxide or lithium hydroxide, is used at a high pH of about 11 to 12, to sever the covalent bonds of the cysteine proteins in the cortex region and recreate these bonds in a relaxed structure of the cortical cells. This process is like taking a structure made from strong beams and reshaping it by reconnecting the beams in a new way. The repeated restructuring of disulfide bonds of the cortical cysteine amino acids can result in substantial damage to the hair over time since the disulfide bonds are broken off completely, and cysteine may be continuously lost as cysteic acid through this process. This loss of cysteine can make the hair age fast and become dull, brittle and weak, leaving the hair dry and unmanageable.

In another system called a perm, also referred to as the non-lye systems, thioglycolic acid and acetic acid mercapto-monoammonium salts are used at a pH of about 8 to 9, to restructure the disulfide bonds of the cortex in a permanent fashion. This system provides a reshaping treatment that is permanent, and can only be grown off by new hair growth, as the hair proteins are modified completely so that they cannot be reversed back to their normal original state. Further, two steps are generally needed for the perm process, and a secondary oxidation phase using a peroxide that stops the disulfide exchange reaction is necessary to stop the reaction of thiolate on the cysteine proteins otherwise the hair will eventually break and fall off completely. These systems also require a set period of application of the solution on the hair so that the amount of interchange of disulfide bonds can be limited, otherwise, once again, the hair will break and fall off.

In the so called "Brazilian" based system, formaldehyde is used to react with the cysteine of the hair, such that the hair cysteine and the formaldehyde will eventually degenerate into a thiazolidine carboxylic acid with very good, although temporary, hair conditioning qualities. Repeated applications via this method will eventually cause a lot of cysteine proteins from the hair itself to be trapped as detached carboxylic acids and hence will depart from the hair as lost proteins, leaving the hair pitted and damaged over time.

In yet another system called the "Keratin Complex" systems, timonacic acid, a thiazolidine 4-carboxylic acid, and its derivatives, are used. In this system of hair renewal and rejuvenation, timonacic acid, which is a condensate of cysteine and formaldehyde, is used as an active agent. This system utilizes the opening of the thiazolidine ring to deliver cysteine proteins to the hair using disulfide bonds. The system works by donating cysteine from keratin proteins and from the thiazolidine or timonacic molecule to the hair, while maintaining a constant supply of keratin proteins to react with the carboxylic groups that result from the donation.

Thus, to modify hair, one must first weaken and break the disulfide bonds of the cortex and allow the proteins to realign into a desired shape and then relock the bonds into the new shape desired by thermal processes or oxidation setting. In almost all these systems, a high concentration of formaldehyde or a carboxylic acid is required to interact with the sulfide bonds and cleave these bonds for introducing new structure to the hair during ironing.

Unfortunately, the dangers associated with the release of formaldehyde and the controversy of whether hydrated formaldehyde in the form of methylene glycol is acceptable in cosmetic products, has not been resolved by the governing bodies that oversee cosmetic products. In fact, in most countries of the world, the use of chemical releasing agents of formaldehyde is restricted to a concentration of 0.2% free formaldehyde in the total solution content.

Though effective, HPLC or high-pressure liquid chromatography, a chromatographic testing technique used by governing bodies to determine the formaldehyde content of cosmetic solutions, has been shown to actually break open the timonacic ring and scavenge the carboxylic group from the molecule to measure formaldehyde as a positive result in the cysteine complex products. Further, the Brazilian systems use raw formaldehyde at a very high concentration, and so, a lot of controversy has been directed at most existing products even though some, like cysteine complex products, do not use formaldehyde in its free form.

None of the known systems utilize nanoparticle technology to encapsulate their active chemical components, rather, known systems are all based on homogenous chemical solutions and blends that are applied to the hair directly.

SUMMARY OF THE INVENTION

One of the main problems that exist with prior art systems is the opening of the hair cuticle to effectuate the delivery of suitable chemistry that would straighten, smoothen and condition hair, and then, closing the cuticle after such delivery so that this chemistry is not lost upon shampooing. The conventional opening of the cuticle using high pH shampoos is effective in opening the cuticle only if the hair remains at an essentially basic pH of about 9 and above. If a conventional product is placed on the open cuticle while at this pH, it does not necessarily close the cuticle and so can be lost during subsequent operations on the hair such as ironing. The present invention illustrates a novel formulation and a novel method of opening the cuticle, and thereafter closing the cuticle only after delivery into the cortex of the active ingredients in the solution that are needed to enter and modify the cortical cysteine proteins. This is achieved by specially designed, packaged, and targeted nanoparticles.

Another problem with existing technologies is that they either require a solution of to be made with a homogenous distribution of a certain percentage of some hazardous chemical, such as, formaldehyde, thioglycolic acid, or ammonium thioglycolate salt, as an active ingredient. Further, these hazardous chemicals are freely dispersed in the solution itself, and are not confined from exposure to a person receiving, or even performing, a treatment. This invention illustrates a new method of packaging active chemicals in specially designed nanoparticles, so that only minimal amounts of active chemicals are freely dispersed in the carrier solution itself.

In all of the known systems, none show how to prepare and manufacture a formulation such as the present invention that allows hair fibers to be reshaped as many times as desired solely by means of heating, and for such reshaped hair fibers not to revert back to their original shape upon washing, without more.

Advantageously, this invention teaches a novel formulation that can be used to reshape hair into a straight or curl configuration, so that washing said hair after such configuration does not revert the hair back to its original shape, and reheating said hair with a styling tool or a blow dryer can cause it to take any other new shape or form as desired.

The cuticle generally opens at high basic pH values, and as such, most treatments are designed at high pH values well above the pH required to open the cuticle. This means that when solutions made of products that are soluble only in acidic conditions are applied to the hair, the hair cuticle closes too quickly and remains closed, thus prohibiting the proper delivery of the straightening, smoothing and conditioning agents inside to the hair shaft cortex. Further, when shampoos and clarifying agents are used to wash the hair after such treatments, the cuticle opens and allows the conditioning agents to dissolve and vanish from the hair. Thus, it would be highly beneficial to provide a new method for the delivery of potential conditioning agents into the hair shaft, while also ensuring that these agents are not lost during subsequent washing of the hair. It would also be useful to control the cortex region of the hair so that the cuticle does not open up constantly when a high pH shampoo is used to clean the shaft. The constant opening of the cuticle delivers harsh shampoo chemicals into the cortex, and also removes and dissolves conditioning agents and other treatments present thereon. Thus existing treatments do not take into account the fact that shampooing makes them ineffective over a few washes. It is therefore important that a treatment that is effective not only opens the cuticle, but also closes it to allow the treatment agents to remain in place on the cortex during their functional lifespan.

To achieve this, the present invention discloses a systematic method to open, close, and subsequently to maintain a treatment agent in the hair, without the use of harsh pH solutions. A generally acidic pH is maintained throughout the present inventive solution, while still allowing the treatment solution to achieve the opening and closing of the cuticle using nanoparticles, as well as to regulate the chemistry within the cortex to achieve all the goals intended by this invention.

To eliminate the present problems of toxicity, smell and other issues, biologically based materials prepared from combinations of chitosan, cross-linked by reductive acetylation of chitin, natural starches, such as corn or pea starch, and a suitable set of proteins including but not limited to arginine, lysine, histidine, and tyrosine proteins and amino acids of collagen are used to generate nanoparticles having a multi-layered structure, within which are encapsulated all the chemistry needed to straighten, smoothen and condition hair, without the need for secondary oxidation processes, or the harsh chemicals associated therewith.

It is a first objective of the present invention to disclose a novel technology for manufacturing and using a treatment and revitalization solution of varying pH values, having microparticles or nanoparticles which act to straighten, smoothen and condition hair, wherein said microparticle or nanoparticle size can be varied to penetrate different regions of the hair shaft through the cuticle layer into the cortex and the matrix regions.

It is a second objective of this invention to make a hair revitalizing, straightening, smoothing and conditioning solution having in suspension, nanoparticles with concentric layers of proteins with progressive values of isoelectric points. As one example, said proteins can be formed as concentric layers of polysaccharides, polypeptides and/or polymeric chains in a nanoparticle in suspension in either an acidic or a basic solution.

In one embodiment, nanoparticles have a first outer polymeric gel layer comprising cuticle opening ingredients in suspension within said first outer polymeric gel layer, and the cuticle opening ingredients are specifically chosen and designed to open the cuticle and allow the nanoparticles to enter the hair shaft cortex region. In one aspect, the first outer polymeric gel layer is made from the isoelectric deposition of said first polymeric gel forming substance, such as chitosan or its derivatives, having a pH approximately equal to its isoelectric point.

One further embodiment comprises nanoparticles having a second inner polymeric gel layer surrounded by said first outer polymeric gel layer, wherein said second inner polymeric gel layer comprises active zwitterion thiolate in suspension within a suitable second polymeric gel forming substance, and said active zwitterion thiolate is specifically chosen and designed to modify cysteine proteins by a process known as thiolate-disulfide exchange. As one example, the second inner polymeric gel layer is made from the isoelectric deposition of a suitable second inner polymeric gel forming substance such as a starch and/or starch derivatives, and said second inner polymeric gel forming substance has a pH approximately equal to its isoelectric point.

In another embodiment, the nanoparticles have a third inner polymeric gel layer comprising cysteine-rich proteins in suspension, said cysteine-rich proteins specifically chosen and designed to donate cysteine and other hair conditioning, revitalizing, and strengthening proteins to the cortex and other regions of the hair. In one instance, the third inner polymeric gel layer has a pH approximately equal to the isoelectric point of cysteine, and is formed via the isoelectric deposition of cysteine and other cysteine amino acids.

It is a third objective of this invention to teach how to make nanoparticles with concentric layers of a cysteine gel core, surrounded by a middle starch layer with embedded oils, thiolate, and emollients, and an outer layer of chitosan, so that, the solubility of the conditioning agents and emollient oils within said nanoparticle matrices remain stable over a long period of time in either a basic or an acidic carrier solution.

It is yet another objective of this invention to disclose a method of creating a hair treatment solution which can open the cuticle, administer chemicals into the cortex for the purpose of straightening, smoothing, and/or conditioning hair using nanoparticles made from concentric layers of chitosan, cysteine, and any of the natural starches, each said layer forming a suspension that has a predetermined pH range and a predetermined set of chemicals, each such set of chemicals designed to perform a specific task on human hair.

It is a further objective of this invention to provide a specifically engineered formulation for a hair thermal straightening and revitalizing treatment comprising nanoparticles with three or more layers, specially designed to encapsulate chemicals at differing pH values at each such layer, wherein, hair straightening chemicals such as (3-mercaptopropyl)trimethoxysilane, 2-mercaptoethanol (BME), isooctyl thioglycolic acid, thioglycolic acid, ammonium thioglycolate salt, an aldehyde and other suitable chemicals can be encapsulated in said nanoparticle matrix and used in a controlled manner without the need for a carrier solution to contain significant amounts of any of the encapsulated chemicals.

It is another intention of this invention to disclose a novel method of straightening, smoothing and conditioning hair, using suspensions of multilayered nanoparticles in zwitterion states that are engineered to close the cuticle by shedding a first reactive outer polymeric gel layer at a pH less than neutral. After entering the cortex region by absorption into the cortex of the hair shaft, the multilayered nanoparticles shed a second layer of polymeric gels carrying thiolate, oils and proteins within said cortex region, and, the multilayered nanoparticles shed a third inner layer of cysteine proteins within said cortex region. Thus, said cysteine proteins and said thiolate are in constant disulfide bond-exchange with cysteine proteins of the cortex region, and the excess cysteine causes a relaxation of disulfide bonds of the cortex region of the hair shaft to modify and relax the hair structure, and to provide a means to straighten, smoothen, and condition hair.

In particular, the invention teaches how to make a hair treatment and hair straightening solution with nanoparticles comprising cysteine, starches, and chitosan. These nanoparticles can be formed with cysteine or chitosan as either a core or a corona. The formulations of the present invention are based on an entirely different premise for restructuring the cortex and the matrix regions of the hair by means of proteins encapsulated in microcontrolled acidic and basic environments, wherein the excess amount of cysteine proteins deposited by the nanoparticle into the cortex region are in a zwitterion equilibrium state and are in constant exchange with cysteine proteins in the cortex, so that the disulfide bonds are in constant state of average flux and are never completely organized in a permanent fashion, thereby leaving the hair relaxed but not permanently changed.

Advantageously, the flux of the thiolate exchange reactions allows the hair to be fashioned solely by heat, so that when washed, it does not revert back to its original shape but remains in the style it was given when last set by a thermal styling tool.

To fully understand the theoretical framework for the present invention, it is important to highlight some properties of the proteins that are utilized.

Cysteine hair proteins comprise a large number of amino acids including, but not limited to, alanine, arginine, aspartic acid, cysteine, cystine, capryloyl hydrolyzed cysteine, glutamic acid, glycine, histidine, hydroxyproline, isodesmosine, isoleucine, leucine, lysine, methionine, phenylalanine, proline, serine, threonine, tryptophan, tyrosine, and valine.

The main component that interacts with the structure of hair is cysteine. The molecular formula for cysteine is $C_3H_7NO_2S$, or $HO_2CCH(NH_2)CH_2SH$. The following is illustrative of two cysteine molecules joined via a disulfide bond, thereby forming cystine, i.e., $(SCH_2CH(NH_2)CO_2H)_2$:

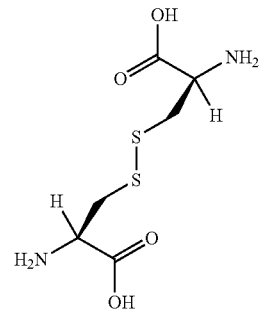 [SMILES: N[C@@H](CSSC[C@H](N)C(=O)O)C(=O)O]

In order to assure full disclosure of the present invention, a discussion of the chemistry involved with at least some of the components utilized to develop this novel technology is believed warranted. The strength of hair, and therefore its shape, is primarily a function of covalent bonds between sulfur atoms in chemical groups referred to as thiolates. Although there are other interactions that can modify hair, thiolates are the main focus of concern for the present invention. Disulphide bonds of the cystines form cysteine proteins in hair. They form alpha-cysteine fibers as polymers, and these polymers represent the major stabilizing covalent links between the polypeptide chains forming fibrous structures in horns, hair, and tusks. This disulfide covalent link in the presence of ionized thiolate groups (—S—) can be used in reactions of the sulfhydryl-disulfide interchange involving ionized thiolate. The disulfide exchange reaction can be used and has been used to relax stress in extended cysteine structures, such as human hair. This interchange favors the breakdown of bonds under stress, and the reformation of new bonds in equilibrium through ionic exchange is the main method that has been used to generate perms and relaxers in the hair industry. The cysteine-thiolate group is nucleophilic and easily oxidized. The reactivity is enhanced when the thiolate is ionized and cysteine residues in proteins have pKa values close to neutrality, so they are often in their reactive thiolate form in solution. This invention utilizes some of the special properties of thiolate, via packaged nanoparticles in acidic and basic environments to modify, straighten, curl, condition and relax human hair.

Since cysteine has disulfide bonds called active thiolate, cysteine can be modified by the thiolate-disulfide exchange, as illustrated below:

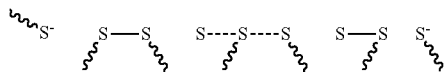

This property of cysteine allows the general shape and structure of hair fibers to be modified by the use of chemicals which affect or break the covalent disulfide bonds between cysteine proteins. It is this disulfide exchange that most lye and perm treatments use to modify the hair structure and its mechanical properties. In perm systems, the reaction is stopped by oxidation, which in some cases is delivered by hydrogen peroxide being placed on the reacting perm. This means that once the thiolate reaction stops, the hair becomes "set" in a permanent fashion in the style it was placed in when the reaction stops. This is an undesirable consequence of perms, which the present invention eliminates.

The present invention comprises chemical agents in a structured solution that is engineered to deliver a specific set of chemicals to a targeted region of the hair shaft without exposing said chemical to the carrier solution itself, and the chemical permits the hair to be formed into different shapes as required by the stylist using only heat energy. Furthermore, the present invention uses an innovative method to manufacture a hair straightening, smoothing, and conditioning system comprising a benign carrier solution within which is suspended packaged nanoparticles, said nanoparticles being made up of gels carrying specific chemicals engineered to interact with targeted areas of the hair shaft.

Keratin is made up of several amino acids, and has the following general form:

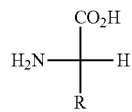

wherein, the R-substituent represents a structural component which varies from one amino acid to another. For example, in the amino acid Proline, R, is a three-carbon chain that joins the nitrogen to the alpha-carbon in a five-membered ring. These amino acids exist in equilibrium between salt formations by a proton transfer from the acidic carboxyl function to the basic amino group. They form ammonium carboxylate structures commonly referred to as a zwitterion state. The zwitterion structure is actually a mixture of ionic states of the amino acid, as a result of its interaction with both acidic and basic solvents. In particular, the amino acids are charged as either positive or negative zwitterion states, and so, the concentration of one type of charge over another is determined by the pKa of the solution. In general, the lower the pH, the more positively charged species one gets in solution. The surface of a protein has a net charge that depends on the number and identities of the charged amino acids, and on the pH. At a specific pH, the positive and negative charges will balance and the net charge will be zero. The pH at which the positive and the negative molecular species are equal is called the isoelectric point, designated as pI. The isoelectric point of cysteine is at about pH 5, and so, in general, cysteine in solution has a net neutral charge at this pH. It is noteworthy that a protein has its lowest solubility at its isoelectric point, due to the fact that if there is a net positive, or negative, charge at the protein surface, the protein preferentially interacts with water molecules in solution, since water is a polar molecule, rather than with other protein molecules in solution. Thus, a net charge makes a protein more soluble. Without a net charge, protein-protein interactions and precipitation of a particulate from solution is more likely. This phenomenon can be used to propagate either charged species away from the solution, or to effectively dissolve the cysteine proteins.

Starches are biodegradable polymers, existing as polysaccharides in plants. They are composed of glucose with glycosidic bonds, the primary components being amylose and amylopectin. Amylose is a planar polysaccharide with the glucose units linked by $\alpha(1\text{-}4)$ glycosidic bonds, while amylopectin is a branched polymer with the glucose units linked as chains of linear $\alpha(1\text{-}4)$ glycosidic units, with $\alpha(1\text{-}6)$ glycosidic linked branches. Thus, starches can be used to form matrices for films and strong biomaterials that can be used as coatings. Simi et al. (Bioprocess and Biosystems Engineering 2007; 30(3): 173-180) describe nanoparticles and their preparation based on starch grafted with fatty acids. Lemarchand et al. (Pharmaceutical Research 2003; 20(8):1284-1292) published on a novel core-shell nanoparticle based on an amphiphilic copolymer. Hornig et al. (Carbohydrate Polymers 2007; 68(2):280-286) describes nanoparticles comprising of dextran esters. Rodrigues et al. (Journal of Controlled Release, 2003; 92(1-2): 103-112) describes the preparation of protein nanoparticles with a hydrophobic poly ε-caprolactone core and a hydrophilic dextran corona. Corn starch is used at least one embodiment, however, pea starch and rice starch would equally work well in the present application. In addition, natural maize starch, degraded maize starch, natural wheat starch, natural potato starch, waxy maize starch, starches from a genetically modified organisms, such as plants, may also be used in the present formulations.

The property of starches to form very good gels and to act as thickeners over specific pH ranges makes them suitable to serve as carriers of a charged thiolate in a suspension as zwitterion states. U.S. Pat. No. 2,389,771, entitled "Explosive Composition" by inventor Kenneth M. Gayer, demonstrates that starches can be used to encapsulate explosive ammonium compounds. Applicant has determined that there is no need to chemically process a starch to absorb a thiolate. Instead, the starch is first heated in a water based solution, stirred properly to a homogenous gel and cooled as a gel. In particular, when starch is mixed and heated with water and oils such as silicone oils, argan oil, wheat germ oil, soy bean oil, olive oils, and with mixtures of one or more thiolates such as 2-mercaptoethanol (BME), isooctyl thioglycolic acid, ammonium thioglycolate and thioglycolic acid compounds such as (3-mercaptopropyl)trimethoxysilane, whose chemical formula is (SHC$_3$H$_6$Si(OCH$_3$))$_3$, and starch-glycolates are formed. The compound (3-mercaptopropyl)trimethoxysilane is readily available in the market from Dow Chemicals, and Sigma Aldrich, and is known to be a very good film former, and has been used in the formation of gold-nanoparticle suspensions as referenced in a paper entitled "Exchange of (3-mercaptopropyl)trimethoxysilane with alkanethiol and co-adsorption on silver powder" by Yihong Wang, Wei Songa, Cunwang Gea, Ning Gua, K. D. Wesche of the Department of Chemistry and Chemical Engineering, Jiangsu Laboratory for Biomaterials and Devices, National Laboratory of Molecular and Biomolecular Electronics, Southeast University, Nanjing, Peoples Republic of China, and the Department of Chemistry, University of Namibia, Windhoek, Namibia.

Another article that references the use of (3-mercaptopropyl)trimethoxysilane for nanoparticle formation is the Euro Nano Forum 2009, Nanotechnology for Sustainable Economy European and International Forum on Nanotechnology. This article shows how the compound can be used for the immobilization of gold nanoparticles onto the inner surface of a fused-silica capillary by applying layers of gold by covalent modification via (3-mercaptopropyl)trimethoxysilane. This compound also accords lubricity and has some emulsifying and humectants characteristics, and it also bonds well to metals to form nanoparticles. The compound has a thiol group at its ends and so it can be readily added and mixed well with the starch proteins to create a homogenous mixture of starch thiolate. Some medicines are coated with sodium starch thiolate, or SSG, a common ingredient in many pharmaceutical pills. SSG is the sodium salt of a carboxymethyl ether of starch. These starch-thiolates are used as rapid disintegrants, to promote the rapid disintegration and release of drugs upon contact with water. The starch-thiolates have an isoelectric point at about pH 6, and so there are ideal for use in hair applications.

Further, the thiols, such as mercaptoacetic acids, are manufactured with sulfur impurities that are very odorous compounds that must be masked by a suitable odor masking agent. However, when such sulfur compounds are absorbed by the starch proteins, their pungent odor can be reduced considerably. Scent oils such as chocolate, coco-mango, cucumber and watermelon, passion fruit, guava, vanilla, lavender, together with powerful odor masking compounds, such as citronella oil, are very effective in reducing the odor of the sulfur compounds. Advantageously, by adding between about 0.5% to about 2.0% by weight of citronella oil and between about 1% to 4% of a suitable perfume or cosmetic scent oil such as one or more combinations of the aforementioned examples, the smell of the sulfur compounds can be reduced to an acceptable level.

In conjunction with odorous mercaptans and thiols, the compound isooctyl thioglycolate may be used to reduce the odor of the sulfur compounds by a considerable amount. However, isooctyl thioglycolate is much more expensive than the regular thiols, and so a combination of isooctyl thioglycolate and other suitable thiols may be used. In at least one embodiment, a combination of isooctyl thioglycolic acid, mercaptoacetic acid, and thioglycolic acid is utilized.

Chitosan is a poly-[1-4]-β-D-glucosamine that is commercially available. It is a derivative of chitin, which is a poly-[1-4]-β-N-acetyl-D-glucosamine obtained from the cell walls of sea crustacean shells, and the wings of some insects. Chitosan is obtained when chitin is deacetylated using a sodium hydroxide (NaOH) solution. The acetylation of chitin to form chitosan has been described in the literature and over the past years, researchers have patented various methods of acetylation of chitin to chitosan. There are generally two types of acetylatable groups for chitin, the N-group, and O-group.

There are no restrictions to the use of either chitin group in the present invention, since the purpose of acetylation is to make the chitosan soluble in acidic solutions. Thus, either acetylated chitosan can be used in the present invention. The following is the general molecular structure of chitosan:

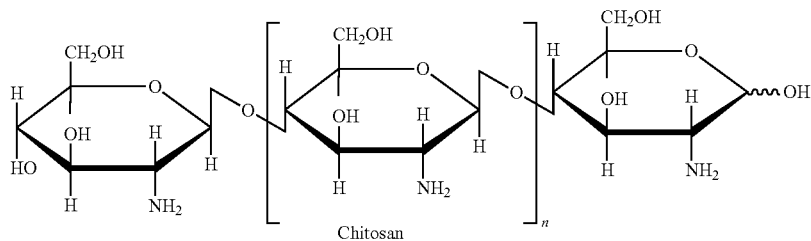

Chitosan

The amino groups allow for the synthesis of different chitosan derivatives (Khan, 2002; Franco, 2004). Chitosan derivatives such as N-succinil-chitosan can be made soluble at much higher pH than the unmodified form. Modified chitosans can be made as described by a methodology proposed by Yamagushi et al, 1981. Modified chitosans can also be purchased from manufacturers such as Solvay LTD or Parchem LLC., and used directly with other ingredients without modification of said chitosan. In one embodiment, an 80% acetylated chitosan is used in the present invention.

Chitosan is soluble in acetic acid and when mixed in hydrated form with amino acids and proteins, it will slowly bond to the amino acid. Thus, a selection of mixtures of cysteine and a small amount of other proteins such as alanine, arginine, aspartic acid, cysteine, cystine, capryloyl hydrolyzed cysteine, glutamic acid, glycine, histidine, hydroxyproline, isodesmosine, isoleucine, leucine, lysine, methionine, phenylalanine, proline, serine, threonine, tryptophan, tyrosine, and valine may be used.

A special blend of cysteine protein carriers is used in the present invention to achieve a full range of interactions with the various parts of the hair shaft. Amino acids such as cysteine peptides are used to permeate the hair shaft and form a thin film over the hair shaft to maintain the shape and rigidity of the fibers of hair. The outer layer of the hair shaft requires a water repellant film to protect it from water penetrating into the matrix to reverse the setting that has been achieved by the solution. Chitosan can be used for this purpose when mixed with pyrrolidone carboxylic acid salt (PMCP) to form a conditioning agent for hair. Most inventions relating to chitosan pyrrolidone carboxylic acids are intended for use as pure conditioning agents or as skin ailment cures. The use of pyrrolidone carboxylic acid salt (PMCP) allows chitosan to emulsify with various types of oils, so that these oils can also be carried as emollients into hair. More particularly, as noted above, chitosan has amino groups which make it water soluble in acidic environments. Thus, while chitosan can dissolve inside the hair cuticle to release starch, oils and cysteine proteins into the matrix, it also acts as a strong bio-adhesive, binding to negatively charged atoms such as the nitrogen or oxygen groups of the hair proteins.

Advantageously, under acidic conditions, the positive charge of chitosan allows it to be highly soluble and thus workable into a fine film from an acidic solution. Thus, a solution being highly acidic is a suitable carrier for soluble chitosan and other film formers. The positive charge of the chitosan molecule is due to protonation of its free amino groups. When chitosan loses this charge, it becomes insoluble in neutral and basic environments.

Chitosan can be carried as a soluble bio-adhesive for both cysteine proteins and other proteins in solution, however, upon delivery to the hair it will slowly become insoluble as the pH of the hair changes with the removal of water and the hair reverts back to neutral pH. Thus, in the present formulation, chitosan acts as a film forming bridge for peptides and proteins in the hair, and the acidity of the solution allows the strength of chitosan-starch-cysteine films to be varied.

The solubility of these films ultimately depends on a complex series of interactions that occur as the solution dries and water is removed from the hair. The film forming ability of the present combination of water, a mixture of hydrolyzed proteins such as cysteine, chitosan, corn starch, and plasticizing agents, such as alcohol sugars of erythritol and glycerol and sorbitol, results in strong flexible transparent films that can be used to coat and protect hair after it is shaped by styling or ironing. Additionally, emollients and conditioners including, but not limited to a combination or a choice from high molecular weight silicones, argan oil, wheat germ oil, soy bean oil, olive oils, and, in at least some embodiments, mixtures of silicone oils together with (3-mercaptopropyl)trimethoxysilane, and Kobo Guard 5400IDD, are added to allow the hair to have gloss and shine as well as acting to protect the hair from UV radiation and humidity. These oils are readily available cosmetic ingredients. In one embodiment, a non-cationic natural food grade *cyamopsis tetragonoloba* gum, such as food grade guar gum, is utilized as a thickener for the present formulation, together with an amount of hydroxyethyl cellulose, oat straw, and xanthan gum. Unlike the prior art, the gum must be natural and processed for food purposes, rather than cosmetic processes, as processed cosmetic grade gum will deteriorate at higher pH values.

A particularly important property of chitosan is its ability to protect hydrophilic macromolecules against degradation. The concentration of NaOH in solution and the time allowed for deacetylation produces differing chitosan molecular weights. Chitosan has a solubility and viscosity that is characterized by the degree of acetylation of chitin. Chitosan is soluble in acetic acid and other acids, and bonds with cysteine and corn amylase to form very strong and stable films over the hair, thus temporarily modifying the physical shape of the proteins in hair. The solubility of chitosan is due to the protonation of free amine groups in the molecule as follows:

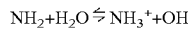

The amino group in chitosan has a pKa value of about 6.5, which promotes protonation in acidic to neutral solution with a charge density dependent on pH. This makes chitosan water soluble and a bio-adhesive which readily binds to negatively charged surfaces. More particularly, zwitterion chitosans can be synthesized by amidation of chitosan with succinic anhydride. The succinic anhydride conjugated chitosan has an isoelectric point which is readily tuned over a pH range of about 4.9 to 9.1. Thus, one can select pH values higher than pH 6 at which the maximum formation of nanoparticles of succinic anhydride conjugated chitosan can be obtained.

Chitosan is insoluble in neutral and alkaline pH and is only soluble in acidic pH. At pH 5 and below, the amine groups are protonated and positively charged, and chitosan is soluble. At a higher pH, however, the polymer loses its charge as amine groups become deprotonated and, therefore, becomes insoluble in water. Cysteine is an amphiphilic protein and its isoelectric point is about 5. At pH values above the isoelectric point of cysteine, i.e., above about pH 5, cysteine is negatively charged and is soluble in water. Thus, mixing chitosan and cysteine together in solution results in simultaneous formation of an insoluble phase, which is due to the formation of chitosan-cysteine coacervation by electrostatic interaction of the negatively charged cysteine protein with positively charged chitosan. The rapid and instantaneous interaction of chitosan with oppositely charged molecules has been reported in the Journal of Pharmaceutical Science, Vol. 78, 1989, pp 964-967, by investigators such as Murali, Prasad, Raman Murthy, Bodmeir and Paraatakul.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which:

FIG. 1 presents Table 1 which lists a range of concentrations, in weight percent, for each ingredient incorporated into at least one embodiment of a hair treatment formulation in accordance with the present invention.

Like reference numerals refer to like parts throughout the several views of the drawings.

DETAILED DESCRIPTION

Figure 2:
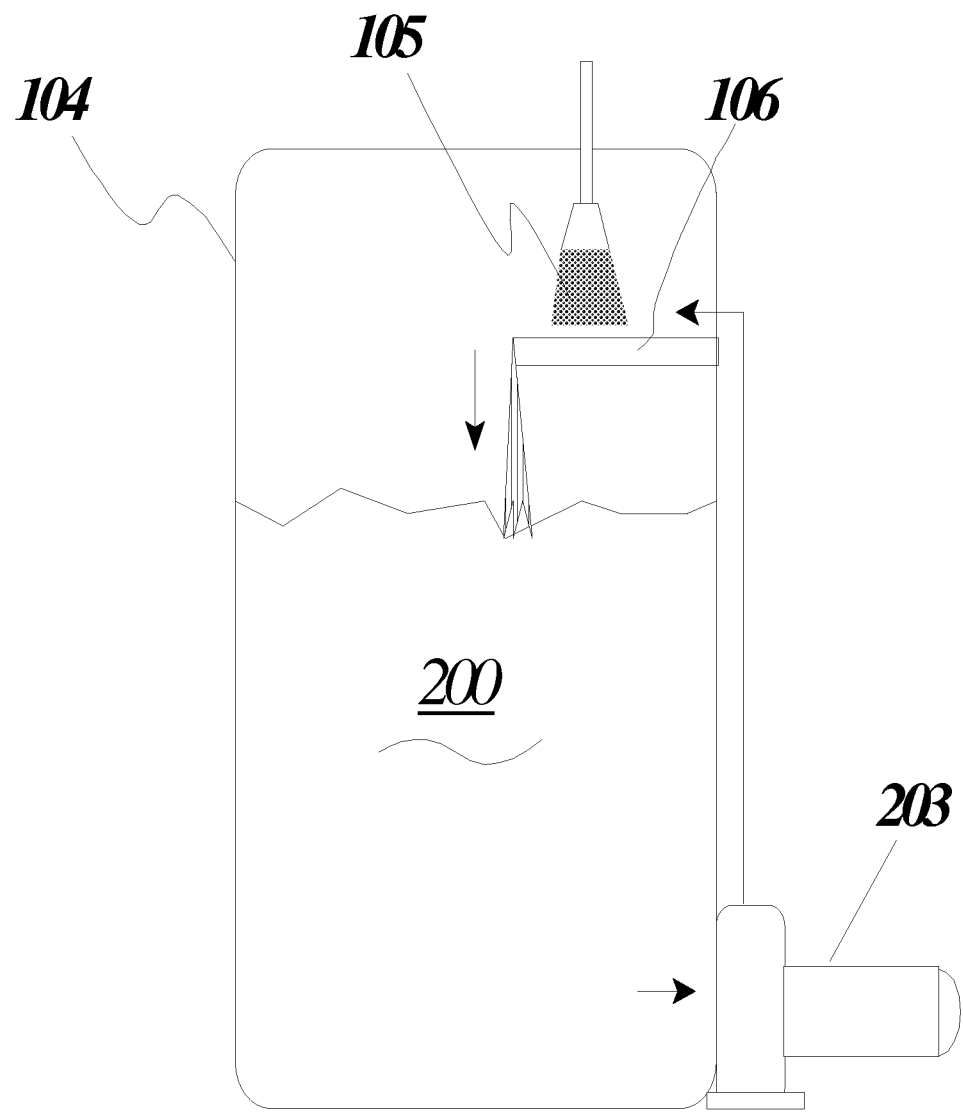
FIG. 2 is a diagrammatic representation of one embodiment of the method of preparation of a hair treatment formulation of the present invention.

As previously described, the opening of the cuticle during shampooing allows many of the treatment components delivered to the hair cortex to simply dissolve and become ineffective after one or more washes. This is due to the fact that the cuticle generally opens only under basic pH conditions, which means that when solutions comprising treatment components that are soluble only in acidic pH conditions are applied to the hair, the hair cuticle closes quickly and severely inhibits or prohibits delivery of the treatment components, such as conditioning agents, to the hair cortex inside of the cuticle. Further, when shampoos and clarifying agents having a basic pH are used to wash the hair shaft, the cuticle opens and allows any treatment components, for example, conditioning agents, which did reach the cortex to dissolve and wash out of the hair. The present invention is directed to a useful and new method for the delivery of treatment components including, but not limited to, conditioning, relaxation, smoothing, straightening, and/or revitalizing agents, into the hair shaft, while also ensuring that the treatment components are not lost during washing of the hair.

To achieve this result, one embodiment of the present invention comprises a novel technique for forming microparticles or nanoparticles having one or more treatment component in a solution, wherein the solution has a variable pH range in order to selectively produce different sizes of microparticles or nanoparticles as needed to penetrate different regions of the hair shaft through the cuticle layer and into the cortex and matrix regions. In at least one embodiment, the present invention is directed to a method of forming composite nanoparticles 100, wherein the composite nanoparticles 100 have a concentric inner layer or core comprising cysteine, which is substantially surrounded by an intermediate layer comprising starch which is selectively embedded with treatment components, for example, conditioning oils and emollients, and an outer polymeric gel layer comprising chitosan. As a result of this multi-layer formulation, the solubility and thus the release of the treatment components embedded in said composite nanoparticle 100, e.g., conditioning oils and emollients, into the hair cortex region can be controlled over a long period of time. The formulations of the present invention are based on an entirely new and novel restructuring of the cortex and matrix regions of the hair via selectively packaged proteins in a controlled acidic or basic micro-environment with film formers, such as cysteine proteins, chitosan, and starch proteins.

In one embodiment of the present invention, a novel solution for revitalization, straightening, and conditioning of human hair is disclosed. In one aspect, an acidic Phase C solution 200 comprises a suspension of composite nanoparticles 100. The Phase C solution 200 is saturated with soluble chitosans, cysteine proteins, starches having a high-amylos content, together with salicylic acid, acetic acid, and/or other reagents to effect acetylation of said film formers to create very fine strong films over hair. The Phase C solution 200, in one further embodiment, comprises a chemical suspension and emulsion of water and oils such as silicones, argan oil, wheat germ oil, soy bean oil, olive oils, and, in at least some embodiments, mixtures of silicone oils, (3-mercaptopropyl) trimethoxysilane, Kobo Guard 5400IDD, as well as gums such as natural non-cationic guar gum, xanthan gum, and agar gum. A small concentration of oxidizing agents may be incorporated into the Phase C solution 200, as needed, to allow reduction of a limited number of the disulfide bonds in the cortex to be "fixed".

FIG. 1 presents Table 1 which lists a range of concentrations, in weight percent, for each ingredient incorporated into one illustrative embodiments of a hair treatment formulation in accordance with the present invention. In at least one embodiment, a hair treatment formulation in accordance with the present invention comprises amino acids, peptides, and proteins which are commercially available from Keratronics Inc., Coral Springs, Fla., and from other vendors around the world such as Croda Inc., and Keratec, LTD. Additional components of the illustrative embodiment of a hair treatment formulation presented in Table 1, are readily available in the market as indicated in table.

As set forth in Table 1, the ingredient deck could vary the viscosity of the hair treatment formulation from a lotion formulation to a gel formulation, depending on the percentage of the ingredients used. More in particular, the viscosity of a hair treatment formulation in accordance with the present invention will correspond to weight percentage of soluble gums and powders that are used.

Method of Preparation.

As previously stated, Table 1 presents ranges of concentrations, in weight percent, for each of the components incorporated into one illustrative embodiment of a Phase C solution 200, in accordance with the present invention. In at least one embodiment, the method of preparing a Phase C solution 200, utilizing the components and the predetermined amounts of each in accordance with Table 1, comprises the following steps. To begin, an amount of water is added to a mixing tank 104, as shown in FIG. 2, wherein the water is at a temperature in a range of between about 70° F. to 120° F. Glacial acetic acid (99.9%) is added to the water to form a Phase A solution, until the pH of the Phase A solution is between about 2.0 and 4.0. The pH of the Phase A solution can be further adjusted by adding an amount of acetyl salicylic acid, which may be provided in a crystalline form.

Once the pH of the Phase A solution is properly adjusted, a portion of the predetermined amount of a mixture of hydrolyzed cysteine and lysine proteins, in accordance with Table 1, is added to the Phase A solution in mixing tank 104, and an amount of hydrogen peroxide or another suitable preservative is added to assure that the Phase A solution remains bacteria and germ-free. Most commercially available hydrolyzed keratin proteins are not suitable for use in the present invention because they contain many proteins with unacceptably high and low isoelectric points. In at least one embodiment, the mixture of hydrolyzed cysteine and lysine proteins further comprises amounts of one or more additional proteins, such as, alanine, arginine, aspartic acid, cystine, capryloyl hydrolyzed cysteine, glutamic acid, glycine, histidine, hydroxyproline, isodesmosine, isoleucine, leucine, methionine, phenylalanine, proline, serine, threonine, tryptophan, tyrosine, and valine.

Next, a predetermined amount of at least one thickening agent is added. In accordance with the illustrative embodiment of Table 1, a small amount of food grade, non-cationic *Cyamopsis Tetragonoloba*, i.e., food grade guar gum, is added to the Phase A solution along with a small amount of agar-agar gum, to increase the viscosity of the Phase A solution until it is about 500 centipoise ("cps"), so as to attain partial thickening of the solution. Next, once the viscosity has been adjusted to about 500 cps, predetermined amounts of emollients and conditioners, namely, silicone oil, argan oil, wheat germ oil, soy bean oil, and olive oil, are added to Phase A solution in the amounts specified in accordance with Table 1. The resultant solution is thoroughly mixed in mixing tank 104 for a period of about one hour per hundred liters of solution, at a speed in the range of between about 1,000 to 2,000 rpm. In at least one further embodiment, Kobo Guard 5400IDD, a thick viscous film forming oil manufactured by Kobo Chemicals Inc., is added in an amount ranging from about 1% to about 5% by weight.

After thorough mixing, amounts of sorbitol and erythritol, which act as plasticizers, are added to the Phase A solution in the mixing tank 104, and an amount of salicylic acid is added to adjust the pH of the Phase A solution to below 4, as necessary, in accordance with Table 1. In at least one other embodiment, a small amount of other proteins, such as collagen, may be added to this mix to increase protein content. This solution is again thoroughly mixed in mixing tank 104 for a period of about one hour per hundred liters of solution, at a speed in the range of between about 500 to 2,000 rpm, until a uniform Phase A solution is achieved.

The viscosity of the Phase A solution is further adjusted to about 800 cps by adding the remaining amounts non-cationic *Cyamopsis Tetragonoloba*, or food grade guar gum, and agar-agar gum, as well as predetermined amounts of special protein mixes such as amp-isostearoyl hydrolyzed soy protein, amp-isostearoyl gelatin/cysteine, and amino acids of lysine, as well as amounts of *abies balsamea* extract and urea peroxide, once again, in accordance with Table 1. The additional proteins tend to thicken the Phase A solution quickly, it is important that the Phase A solution continue to mix well in the mixing tank 104 at a speed in the range of between about 500 to 2,000 rpm while these additional proteins are added to tank 104.

The pH value of the Phase A solution will increase as some of the aforementioned gums and oils are added, and as such, adjustment is needed and effected by adding additional amounts of salicylic acid until the pH of the Phase A solution is once again below 4. Addition of the salicylic acid and acetyl salicylic acid increases the acidity and generally increases the ionization potential of the peptides in the Phase A solution.

At this point, the remainder of the predetermined amount of hydrolyzed cysteine and lysine proteins is added into the mixing tank 104 containing the acidified Phase A solution. This will slightly increase the pH of the Phase A solution.

The Phase A solution is then mixed for a period of time so as to assure complete dissolution of each of the components. In general, when the Phase A solution is thoroughly mixed at an acidic pH, the mixture of the cysteine proteins and other peptides becomes soluble and the particle size of the cysteine proteins and other peptides in suspension in the Phase A solution is in the order of about 50 microns. At this point, the Phase A solution is allowed to sit and settle in the mixing tank 104 until any aggregate has settled to the bottom of the tank 104, which generally occurs in a period of time in the range of between about five to twenty-four hours. The aggregate can then be removed by filtering. A 100 micron mesh filter may also be used to remove any suspended particulates from Phase A solution. It is important that the mixing tank 104 be designed with a bottom tank-suction pump 203 which recirculates the Phase A solution to a trough 106 inside the tank 104. Further, it is important that the tank 104 is a plastic or other suitable electrically insulating material so that electrical charges are not transmitted into the Phase A solution by the material of construction of the mixing tank 104.

After settling and filtering, a mist 105 of a 50% sodium hydroxide solution, or an equivalent base, is sprayed into the trough 106 of the mixing tank 104 at the rate of about 0.5 gram per minute per 100 liters per minute of the Phase A solution being recirculated through the trough 106, to gravitationally fall as a mist 105 unto the Phase A solution as it is recirculated through the trough 106. The base spray mist 105, having a droplet size in the range of about 50 microns or less, will form small regions of high pH of about 11 in the generally acidic environment of the Phase A solution, i.e., small regions will have a pH which is greater than the isoelectric point of the cysteine proteins and other peptides. As such, the cysteine proteins and other peptides will emerge as mainly negatively charged nanoparticles in the Phase A solution, which will form an inner layer or core 101 of composite nanoparticle 100, as shown in FIG. 3. The inner core 101 will comprise proteins, primarily being cysteine but also including arginine, lysine, histidine, tyrosine, cysteine and lysine proteins, while leaving other proteins that are soluble at the high pH in the effected regions in solution. Thus, it is important that the hydrolyzed cysteine and lysine proteins utilized in the present invention are rich in cysteine proteins so as to effectuate the maximum number of composite nanoparticles 100 that will form in the Phase A solution.

Further, in at least one embodiment, the exact proteins that will form the inner core 101 of the composite nanoparticles 100 can be fine-tuned by adjusting the pH of the base spray mist 105. If only cysteine proteins are desired, then the pH of the base spray mist 105 should be no more than the pH of the isoelectric point of cysteine, i.e., a pH of about 5 to 5.5. However, since the thiol-disulfide exchange is inhibited at pH values below 8, it is important that this nano-region have a pH greater than 8, since an interaction of a thiol at a pH higher than 8 within this nano-region will result in the de-protonated thiolate from acting on a thiol-disulfide exchange.

Thus, utilizing the present invention, it is possible to maximize the cysteine protein content in the inner core 101 of the composite nanoparticles 100 by predetermined selection of the cysteine source and adjustment of the pH of the base spray mist 105. The inner core 101 will be formed of proteins, comprising primarily cysteine along with other proteins including, but in no manner limited to, arginine, lysine, histidine, and tyrosine, while leaving other proteins that are soluble at the high pH in the effected regions in solution.

The cysteine proteins that form the inner core 101 of the composite nanoparticles 100 in the Phase A solution are a net mix with an average positive charge and exist in zwitterion states embedded in an acidic neighborhood of the Phase A solution. Since the proteins form gels around the nuclei in the higher pH spray droplet regions, the effect of the acidic Phase A solution on the nanoparticle region of proteins is limited by the Liesegang phenomena, which causes periodic layers of small amounts of the gum proteins and mainly the cysteine proteins to form a highly viscous globular nucleic particle of gel. Thus, by adjusting the time for this process to occur, composite nanoparticles 100, with cysteine nuclei, or inner cores 101, of any desired size can be formed.

A starch solution is prepared in a separate mixing tank containing ten parts water to one part starch, for example, corn starch, in an amount as specified in Table 1, to prepare a Phase B solution. The Phase B starch solution is heated and mixed well to generate a weak gelatin. The property of starches to form very good gels and thickeners at specific pH ranges makes them suitable to participate as carriers of the charged thiolates in a suspension as zwitterion states. The thiolates which may be utilized in the present invention include, but are not limited to, any of the mercaptans, dithioerythritol, (DTE) glutathione, β-mercaptoethanol, tris(2-carboxyethyl)phosphine, 2,2',2"-phosphanetriyltripropanoic acid, acetic acid mercapto-monoammonium salt, isooctyl thioglycolic acid, and thioglycolic acid. In at least one embodiment, a cross-linking molecule such as an aldehyde that may cause a thiol-disulfide exchange to occur can be utilized instead of a thiol. In accordance with the illustrative embodiment of Table 1, oat straw powder is used in addition to the starch to form good and strong film with this mixture of proteins, even at low concentrations, and it can also be used in conjunction with chitosan, other starches, and cysteine to form a good matrix for keeping oils and emollients intact on hair.

In one embodiment of the present invention, the starch/water solution is heated to a temperature in the range of between about 100° F. to 180° F., then thoroughly mixed at a speed in the range of between about 500 to 2,000 rpm for a period of between about two to five hours per 1,000 liters of solution to form a homogenous Phase B solution, which it then allowed to cool to about room temperature.

Once cooled, predetermined amounts of (3-mercaptopropyl)trimethoxysilane, isooctyl thioglycolic acid, and thioglycolic acid are added to Phase B solution, and mixed well at a speed in the range of between about 500 to 2,000 rpm for a period of between about two to five hours per 1,000 liters of solution, until a homogenous starch-thiolate in Phase B solution is obtained. Some medicines are coated with sodium starch thiolate, or SSG, a common ingredient in many pharmaceutical pills, wherein the SSG is the sodium salt of a carboxymethyl ether of starch. These starch-thiolates are used as rapid disintegrants, i.e., to promote the rapid disintegration and release of drugs upon contact with water. The starch-thiolates have an isoelectric point of about pH 6, and as such, are ideal for use in hair applications.

The thiol-disulfide exchange is inhibited at pH values below about 8, where the protonated thiol form is favored over the de-protonated thiolate form. Thus, protonated thiols do not undergo a thiol-disulfide exchange with the starch proteins in solution at the pH of the starch isoelectric point, i.e., at a pH of about 6. In at least one embodiment, the pH of the starch-thiolate mixture in the Phase B solution has a potential lower than the pH of the isoelectric point of cysteine and the starch itself, which is about pH 5.5, so that the net charge of the starch proteins in the Phase B solution will be negative. In such an embodiment, the starch proteins in the Phase B solution will have a net negative charge that can attach to the cysteine proteins in the Phase A solution, which will have a net positive charge, since the cysteine proteins reside in a net basic pH of 9 or more, i.e., the cysteine proteins exist at a far greater positive potential than their isoelectric points. The pH of Phase B solution can be regulated by adding salicylic or acetylsalicylic acid as needed. The starch-thiolate mixture, i.e., the Phase B solution, is then added to the acidic Phase A solution in mixing tank 104, which has also been cooled to room temperature. In the present illustrative embodiment, the total amount of water, starch, (3-mercaptopropyl)trimethoxysilane, isooctyl thioglycolic acid, thioglycolic acid, hydrolyzed cysteine and lysine proteins, and the other components previously noted, are as specified in Table 1, and care must be taken to ensure that the amount of each component present in the combined Phase A-Phase B solution is within the range specified therein.

At least one embodiment of the present invention includes the step of vigorously mixing the Phase A solution combined with the Phase B solution at a speed in the range of between about 500 to 2,000 rpm for a period in the range of between about five to twelve hours per 1,000 liters of combined solution. After mixing, the pH of the combined solution is generally in the range of about 4, which is less than the isoelectric point of the cysteine and less than the isoelectric point of the starch-thiolate.

The combined solution is then left to stand for a period of time which is determined by the total quantity of the combined solution. As one example, a 1000 kg batch of combined solution should be left standing for at least two hours, but no more than four hours. The time may be reduced by more than half by heating the solution slightly to about 120° F. The step of permitting the combined solution to stand allows for ionic interactions to cause an intermediate layer 102 of starch-thiolate to form around the cysteine nuclei, or inner core 101, in suspension in the combined solution. The profile of the intermediate nanoparticles change as the starch thiolate attaches itself to the inner core 101. Thus, intermediate nanoparticles having a protein nucleus or inner core 101 and a starch-thiolate mantle or intermediate layer 102, are formed in combined solution. The particle size of the intermediate nanoparticles in the combined solution at this point are on the order of 75 to 100 microns. The pH of the combined solution will in general remain at about 4, however, the pH at the inner core 101 comprising the cysteine nucleus of the composite nanoparticles 100 will remain in the range of a pH of about 9 or more.

The method for preparation of composite nanoparticles 100 in accordance with the present invention further comprises the step of adding a predetermined amount of chitosan to the combined solution 200 at room temperature, thereby forming a Phase C solution 200. In at least one embodiment, the amount of chitosan is as specified in Table 1, and in at least one further embodiment, the chitosan is added in the form of a chitosan powder. Non-modified chitosan is only soluble under acidic conditions, specifically, at a pH of 5.5 or less. As such, when non-modified chitosan is added to combined solution having a pH in the range of about 4, the chitosan will dissolve since the pH of the solution is lower than 5.5. In at least one embodiment, pyroglutamic acid ("PCA") is added to the Phase C solution 200 to help emulsify the chitosan and promote cross-linking with the starch and cysteine proteins of the composite nanoparticles 100. In at least one further embodiment, pyrrolidone carboxylic acid is utilized instead of PCA. If the final Phase C solution 200 is required to be acidic for good hair conditioning quality, then, it is important that the pH be more than the isoelectric point of the chitosan to give it a positive net zwitterion state, however, it is undesirable to have the pH greater than about 9.

If the Phase C solution 200 is brought to a pH slightly more than the isoelectric point of the chitosan, such as by adding sodium hydroxide or another suitable base, then, the chitosan will acquire a zwitterion state with a net positive charge. In this zwitterion state, the chitosan will form an electrolytic outer layer 103 of positive charges around the nucleating negatively charged starch-thiolate intermediate layer 102, which surrounds the protein inner core 101.

Figure 3:
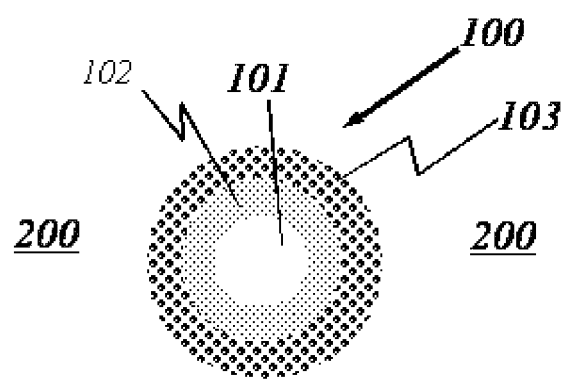
FIG. 3 is illustrative of one embodiment of a composite nanoparticle in accordance with the present invention.

Thus, composite nanoparticles 100 are formed in the Phase C solution 200 having an outer layer 103 comprising a polymeric chitosan gel, an intermediate layer 102 comprising starch-thiolate components, and an inner core 101 comprising cysteine-rich proteins and other proteins. FIG. 3 is illustrative of one embodiment of a composite nanoparticle 100 in a Phase C solution 200.

Once the Phase C solution has been prepared in accordance with the foregoing procedure, perfume and/or scent, as well as citronella oil may be added to the Phase C solution, with mixing, in accordance with the amounts listed in Table 1.

The Phase C solution 200 prepared in accordance with the foregoing method will have an acidic pH of about 5.5, and will carry packaged composite nanoparticles 100 having localized higher pH values. Specifically, the outer layer 103 of polymeric chitosan gel formed on the composite nanoparticles 100 in suspension, protects the internal environment of the composite nanoparticles 100, i.e., the intermediate layer 102 and inner core 101, such that these layers are not readily influenced by the pH of the Phase C solution 200. Thus, even if the pH of the Phase C solution 200 is increased, a pH gradient that has been achieved inside the composite nanoparticle 100 becomes a maximum at the isoelectric point of chitosan. The relationship between pH of the Phase C solution 200 and the net isoelectric charge in each layer of a composite nanoparticle 100 prepared in accordance with the present method is illustrated in the following table.

| Region | pH | CHARGE |
| --- | --- | --- |
| Cysteine gel layer | pH > Isoelectric point of Cysteine | + |
| Starch-thiolate layer | pH < Isoelectric point of starch | − |
| Chitosan gel layer | pH > Isoelectric point of chitosan | + |
| Phase C solution 200 | pH > Isoelectric point of chitosan < 7 | |

In at least one embodiment of the present invention, the chitosan utilized is a chemically modified derivative of the biopolymer added to Phase A solution, which allows the equilibrium or center point pH that acts as barrier between the outer layer 103 and the inner core 101 of the composite nanoparticle 100 to be adjusted. More in particular, the succinic anhydride attached to the free amino groups present along the chitosan polymer chain imparts to the molecule different physicochemical properties not exhibited in non-modified chitosan. This enhances the solubility of the modified chitosan in slightly acid, neutral and alkaline media, due to the long alkyl chains attached to hydrophilic parts. In one instance, the hydrophilic portion of D-glucosamine promotes stronger interactions with the water molecules, and consequently, enhances the solubility of the chitosan polymer.

As one example, chitosan derivatives such as N-succinil-chitosan can be soluble at a pH of between 7 and 9, well above that of the non-modified chitosan. Thus, a basic form of the Phase C solution 200 may be obtained utilizing modified chitosans instead of the non-modified chitosan. In such an embodiment, additional amounts of a base, such as sodium hydroxide or potassium hydroxide, may be added to Phase C solution 200 to increase the final pH of the solution to a range of between about 8 to 9. Thus, a modified chitosan may be utilized to fix or set the internal pH of the composite nanoparticle 100 to some maximum value equal to or less than the isoelectric point of a modified chitosan. By way of example, utilizing a modified keratin having high concentrations of cysteine (pI=5.0), with amounts of arginine (pI=10.8), lysine (pI=9.8), histidine (pI=7.6), tyrosine (pI=5.7), glutamic acid (pI=3.2), and/or aspartatic acid (pI=3.0), one could selectively cause the formation of an outer layer 103 of the composite nanoparticle 100 which comprises a protein of choice. It is important to note that the present invention is not limited to chitosan or its derivatives. In fact, any suitable bio-polymer or organic polymer may be utilized.

Thus, the method of the present invention allows for the formulation of two distinct embodiments of composite nanoparticles 100 in a Phase C solution, namely, an acidic formulation and a basic formulation of the Phase C solution 200. This permits application of the composite nanoparticles 100 of the present invention to serve as a carrier for a wide variety of hair treatment components under pH conditions ranging from a pH of 3 to a pH of 12.

In an embodiment of the present invention comprising a basic Phase C solution 200, the cuticle of the hair is directly opened when the Phase C solution 200 contacts the hair. This provides the advantage of controlling the opening of the cuticle using the high pH of the Phase C solution 200, and the pH of the outer polymeric gel layer 101 of the composite nanoparticle 100. Further, when the composite nanoparticle 100 enters the cuticle, it delivers the thiolates and the cysteines at an a pH which is lower than the pH of the Phase C solution 200, so that when the solution dries and dehydrates on the hair shaft, the internal pH of the composite nanoparticle 100 effects the cuticle, causing it to close.

It is important to note that the zwitterion states of the thiolates acting in the presence of excess of cysteine disulfide bonds leave room for the hair to be reshaped easily, since it is totally relaxed. More in particular, the average bond energy of the un-set thiol-disulfide exchange makes it possible to shape the hair using heat only. Stated differently, the ionic bonds of the hair are not strong enough to restructure the hair into its original treated shape, but reheating and re-ironing can reshape the hair fibers easily. Further, if the hair is reshaped, it will not revert back to its previous shape when washed. Thus, an unlimited amount of styling can be performed, each of which will not be reverted by washing the hair, but can only be reshaped by a styling tool.

Method of Use.

As stated above, a Phase C solution 200 may be prepared in accordance with the present invention to serve as a carrier for a wide variety of hair treatment components including, but not limited to, conditioning, relaxation, smoothing, straightening, and/or revitalizing agents. The present invention further discloses a method of hair treatment utilizing a Phase C solution 200 comprising a plurality of composite nanoparticles 100 which serve as carriers for one or more predetermined hair treatment component(s).

In one embodiment of the present treatment method, a user's hair is first washed with a clarifying shampoo that has a high pH value greater than 8.5. This cleans off all the oils and allows the cuticle to open wide. Generally, three washes are required to make the hair shafts completely oil free. The hair remains at a general pH value in the range of between about 6 to 8 , until a Phase C solution 200 is put on the dried hair. In one embodiment, the user's hair is dried with a blow dryer, and then the Phase C solution 200 is brushed evenly into the user's hair. It is important that the Phase C solution 200 saturate the hair completely, with the excess removed by combing through the hair. After application, the hair may be immediately dried again using a blow drier, or it may be allowed to dry naturally.

In an embodiment of the present treatment method utilizing a Phase C solution 200 having an acidic pH, when the composite nanoparticles 100 enter the cuticle, the cuticle closes due to the fact that the pH of the outer polymeric gel layer 103 of the composite nanoparticles 100 is acidic. Thus, chitosan and other treatment components are delivered into the cuticle in a soluble form, and the composite nanoparticles 100 will then penetrate the cortex and enter into the matrix region of the hair to react with hair protein fibrils, which are encased in globular charged proteins. Since the composite nanoparticles 100 are encapsulated in an acidic environment, hydrogen bonds are broken when the water molecule ions of hydrogen and oxygen are attracted and interacted with charged regions of proteins in the matrix, that are held together hydrogen bonds. Further, the negatively charged nitrogen atoms in chitosan and other proteins form strong ionic bonds with hydrogen attached to protein molecules of the cysteine proteins of the hair, to form solid and rigid structures. Thus, upon introduction of an acidic Phase C solution 200 of this embodiment of the present invention, nitrogen bonds in the matrix region are weakened and attach to the liquid hydrogen ions of the Phase C solution 200, and as a result, the matrix region of the hair becomes placid and fluid instead of solid.

As noted above, the cuticle re-closes when the composite nanoparticles 100 are released into the cortex region since the cysteine proteins in the inner polymeric gel core 101 are in a basic environment, thereby trapping the treatment components inside of the closed cuticle, proximate the cortex and the matrix regions. Drying and removal of water from the Phase C solution 200 that has penetrated the cuticle, results in the pH of the hair being dominated by the internal chemistry of the composite nanoparticles 100. Thus, as the Phase C solution 200 dries, the pH of the hair increases from the initial acidic pH of the Phase C solution 200, and leaves the composite nanoparticles 100 in a basic pH environment in the cortex. The reduction of the water content of the Phase C solution 200 causes the composite nanoparticle 100 chemistry to dominate the environment of the cuticle, resulting in a high pH, and thus opening the cuticle to deliver starch-thiolate and cysteine proteins to the cortex. The thiolates effectuate a disulfide-exchange reaction that causes the disulfide bond of the cortex to exchange with the cysteine proteins in the composite nanoparticles 100. The bonds are not completely broken, since there will be an excess of cysteine to donate sulfur bonds. This excess of cysteine causes a continuous resonation of the disulfide exchange between cysteines in a zwitterion balance.

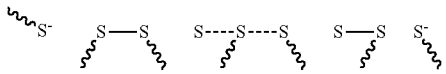

The cortex remains relaxed as the structure of the bonds becomes statistically indeterminate as a finite mechanically rigid structure. The general reactions can be broken into two steps. The following is representative of the first step of the reaction.

cysteine—S—S-cysteine+2(R—S—H)=2(cysteine-S—H)+R—S—S—R (cystine)+(mercaptan)=(reduced cysteine)+(disulfide)

The above reaction occurs between the starch-thiolate phase and the free cysteine present in the Phase C solution 200, as opposed to cysteine embedded in the inner core 101 of the composite nanoparticle 100, to form reduced cysteine. Unlike perms, no oxidation phase is required to stop the reaction. Instead, the abundance of cysteine in the cortex region allows an exchange reaction between the hair cysteine and the solution cysteine to form cystine as a new bond, thereby "setting" the hair. However, since this exchange does not involve an irreversible setting by oxidation, such as via hydrogen peroxide, the cystine bonds can be reconfigured with heat energy to reconstitute new bonds of minimal stress in a new shape. Thus, the second step of the reaction is to reverse the process and regenerate cystine from the hair proteins themselves.

2(cysteine-S—H)+R—S—S—R=cysteine-S—S-cysteine+2(R—S—H)(cysteine)+(disulfide)=(new bonded cystine)+(mercaptan)

The equilibrium between the two reactions keeps an ephemeral bond between the cysteine proteins making it possible to reform the bonds and reshape the hair solely upon expose to a source of heat energy. Since the thiolate-disulfide exchange is influenced by heat, the energy of the bonds is only on average reduced when heat is applied and the exchange becomes rapid. During this period, the hair is vulnerable to changes in shape which can be effectuated by ironing or by intense blow drying to the desired change of shape. The thiolate and cysteine proteins of the composite nanoparticles 100 which are present at saturation levels within the cortex are not readily dissolved in water during subsequent washing of the hair, since the chitosan outer layer 103 of the composite nanoparticles 100 is insoluble at high pH values. However, over time and numerous shampooing, the composite nanoparticles 100 and the embedded cysteine proteins will be washed from the cortex region, and the hair will revert back to its natural state.

The modification of hair utilizing the method of the present invention can not be classed as a perm or a normal cysteine treatment as per prior art. It is in fact a new and novel method of modification of the hair brought about by ironing and blow drying, or other appropriate heat treatment, without the loss of such modifications due to water absorption into the cortex and the matrix region of the hair. In fact, the present method allows a user to modify the hair into as many shapes as the user desires during the efficacious period of the treatment. Each modification can only be accomplished by ironing or by blow drying with intense heat, and hot water from shampooing and washing does not undo the modification or the pattern in which the hair has been "set". Further, unlike a perm, the hair can be simply "reset" into a new modified shape upon application of a sufficient amount of heat energy.

In accordance with at least one embodiment of the present invention, the temperature at which the hair can be temporarily "set" can be varied, depending on the pH of the Phase C solution 200, and the concentration of cysteine that is stored in the inner core 101 of the composite nanoparticles 100. In general, the greater the quantity or concentration of cysteine in the composite nanoparticle 100, the lower the "set" temperature will be. Further, the higher the pH of the inner core 101, the lower the "set" temperature, as well as the "set" time, will be. In general, a thirty to forty minute period of heat treatment at a temperature of about 300° F., such as, via a heating iron, is adequate to generate a good "set" for an average head of hair.

During the useful life of a treatment application, the gums, acetyl salicylic acid and salicylic acid also remain on the hair as fine films that keep the pH of the hair shaft controlled at pH values at about the isoelectric point of the governing outer layer of the composite nanoparticle 100. Thus for chitosan, the pH will be around 5 to 6, keeping the cuticle closed and smooth. Meanwhile, the chitosan-starch-cysteine particles delivered into the cuticle remain as conditioning agents for a long period of time, without dissolving. Further, since the solubility of the chitosan, cysteine and starches is minimal at high pH values, some of these proteins and acids, are dissolved in the Phase C solution 200 itself, and remain as fine protective films around the hair shaft when the hair is dried and ironed, such as via a styling tool.

The concentration of composite nanoparticles 100 in the Phase C solution 200 determine the ratio of its film forming ability for smoothness and shine of the hair, and the ability of the solution to modify hair shape. The higher the concentration of composite nanoparticles 100, the more modifying ability the Phase C solution 200 will have. This makes it possible to make solutions of differing degrees of "inside" cuticle and "outside" cuticle actions. In general, the composite nanoparticles 100 of a Phase C solution 200 having a more basic pH will exhibit a greater degree of action of "inside" the cuticle. This is due to the fact that when hair is treated with a Phase C solution 200 having a basic pH, the treatment components embedded in the composite nanoparticles 100 of the solution are slowly released as the pH of the hair rises to normal pH, allowing the chitosan-starch-cysteine mixture to remain as stable composite nanoparticles 100 encapsulated in a generally acidic environment inside the cuticle. Failure to properly protect the chitosan, cysteine and oils of the Phase C solution 200 from the generally neutral to acidic environments of the hair during bathing, or shampooing, such as is accomplished by providing composite nanoparticles 100 in a Phase C solution having a basic pH, permits rapid loss of these treatment components from the cuticle of the hair. Thus, the particle size, and the protection accorded by the chitosan and starch proteins is critical in making the effects of the Phase C solution 200 last much longer than is currently possible using existing delivery technologies of these proteins.

At least one embodiment of the present invention provides a method for hair revitalizing, conditioning, and straightening utilizing a Phase C solution 200 that reacts with the outer and inner cuticle of the hair protein fibrils, which are encased in globular proteins, generally referred to as the matrix. The present invention discloses one embodiment in which a Phase C solution 200 comprising of reagents are designed to interact with sulfide bonds in the matrix, without the destruction of said bonds, and thus, will allow changes in the general shape of the cortex of the hair shaft without breaking these bonds permanently. The Phase C solution 200 works by first allowing the cuticle to open, by nature of the high or basic pH of the Phase C solution, and then by delivering composite nanoparticles 100 to the cuticle which have different, i.e., lower, pH values than the pH of the Phase C solution 200 itself. Thus, a payload of acidic composite nanoparticles 100 having one or more treatment components embedded therein can be delivered to the cortex and matrix regions of the hair by a Phase C solution 200 having a basic pH, which is suitable for opening the cuticle, and re-establishing the amorphous dislocation of the matrix proteins of the hair due to rearrangement of ionic hydrogen bonds that cross-link the said matrix proteins.

In at least one embodiment, the degree of alkalinity of the Phase C solution 200 determines the longevity of the treatment. In general, negatively charged nitrogen atoms form strong ionic bonds with hydrogen attached to protein molecules to form solid and rigid structures. However, upon introduction of a Phase C solution 200 having a basic pH to clean hair, in accordance with the present invention, nitrogen bonds in the matrix region are weakened and become attached to the liquid hydrogen ions of the Phase C solution 200, and so, they become placid, and fluid, instead of acting as a solid and rigid structure. The protein-liquid phase of the reactions allow restructuring of the matrix of the hair to form new hair styles and shapes, such as straightening, without the need to break sulfur bonds permanently. Ironing, or other applications of heat energy, reacts with the Phase C solution on the hair to create a thin transparent protective film of chitosan-cysteine and corn starches over the hair shaft, and after moisture is removed from the matrix and the cuticle, and causes the hair shaft to reshape and reconstitute the matrix to a desired configuration. The matrix becomes rigid again as water is removed from the hair.

The outer polymeric chitosan gel layer 103 of the composite nanoparticles 100 can be formed to have a pH greater than 9, or less than 6, so that when basic, it acts to open the cuticle, and when acidic it acts to close the cuticle. The intermediate layer 102 of the composite nanoparticles 100 comprising starch-thiolates, allow embedding of thiolates, oils, and emollients to provide advantageous delivery of said oils and emollients to the to the cortex and matrix regions of the hair, without loss to the ironing or drying process.

Thus, the present invention discloses a new and novel method for hair revitalization and reshaping, comprising strong film forming agents in the form of a Phase C solution 200 comprising composite nanoparticles 100 having hydrolyzed cysteine peptides and suspended composite of chitosan, corn starch, cysteines, together with acetyl salicylic acid, acetic acid, agar gum, and other reagents for acetylation of said film formers, and to create very fine and strong films over hair. The chitosan-corn starch-hydrolyzed cysteine peptide treatment components are embedded in composite nanoparticles 100 suspended in an emulsion in the Phase C solution 200, along with oils, such as silicones, (3-mercaptopropyl) trimethoxysilane, Kobo Guard 5400IDD, which are acidified with acetyl salicylic acid and acetic acid and thickening gums such as natural guar gum, xanthan gum, and agar gum which act as conditioners and emollients. A small amount of an oxidizing agent allows reduction of open sulfide bonds to be fixed as needed.

While the use of non-conditioning nanoparticles as carriers of emollients to the hair is known, such treatment methods utilize nanoparticles to act as electrolytic carriers of proteins, oils, and emollients, that add value to the conditioning of the hair. These previously known nanoparticles serve solely as external carriers of emollients and are not sacrificial carriers since, in general, they do not physically participate in hair interactions, i.e., opening and closing of the cuticle, or in film formation. The present invention discloses a method of using treatment components which act as their own pre-packaged sacrificial carriers in solution, by selectively embedding the desired treatment components into composite, multi-layered composite nanoparticles 100. These sacrificial carriers are not only a part of the Phase C solution 200, they are packaged composite nanoparticles 100 that comprise the very emollients and conditioning proteins that are being used to control and condition the hair. One significant advantage of the present invention is that the pH of the Phase C solution 200 can be different from the pH of the composite nanoparticles 100 which it carries, and this pH difference can be manipulated to any desired pH value within the ranges of about pH 3 to about pH 12. As such, the present invention permits the preparation of a continuous class of protein carriers that can be used for various hair types and uses. These hair types can have different cuticle sizes and opening capability, and the industry generally has to make a variety of products for user's having bleached hair, damaged hair, as well as virgin or untreated hair types.

As one example, if the pH of the Phase C solution 200 is brought to about 8.5, micro-gelation can be homogenized by proper mixing to create a uniform basic Phase C solution 200 with a basic micro-environment carried as localized composite nanoparticles 100. Thus, advantageously, if the environmental carrier Phase C solution 200 is made acidic, one could deliver into the cuticle of the hair not only chitosan, cysteine and starch proteins, via composite nanoparticles 100, but one could at the same time also deliver these same proteins as dissolved proteins in the acidic environment of the Phase C solution 200 itself, to serve as film formers. This makes it possible for composite nanoparticles 100 to act "inside" the cuticle, and at the same time act as film-forming solutions of chitosan-cysteine-starch that protect the "outside" of the hair. Thus, the best of both worlds is achieved by the present invention. As such, the pH of the Phase C solution 200 can be adjusted to increase the longevity of the Phase C solution 200 on hair and generate either a temporary or a semi-permanent heat re-shapeable hair straightening and smoothing treatment.

While the invention has been described, disclosed, illustrated and shown in various terms or certain embodiments or modifications which it has assumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A hair treatment formulation, said hair treatment formulation comprising:
   a plurality of composite nanoparticles suspended in an amount of a solution,
   at least some of said plurality of composite nanoparticles having an inner core, an intermediate layer, and an outer layer, each said inner core comprising a predetermined amount of at least one protein, and wherein said intermediate layer comprises a predetermined amount of at least one thiolate.

2. The hair treatment formulation as recited in claim 1 wherein said at least one protein is selected from the group consisting of cysteine, lysine, alanine, arginine, aspartic acid, cystine, glutamic acid, glycine, histidine, hydroxyproline, isodesmosine, isoleucine, leucine, methionine, phenylalanine, proline, serine, threonine, tryptophan, tyrosine, and valine.

3. The hair treatment formulation as recited in claim 1 wherein said inner core comprises a plurality of proteins.

4. The hair treatment formulation as recited in claim 3 wherein said plurality of proteins are selected from the group consisting of cysteine, lysine, alanine, arginine, aspartic acid, cystine, glutamic acid, glycine, histidine, hydroxyproline, isodesmosine, isoleucine, leucine, methionine, phenylalanine, proline, serine, threonine, tryptophan, tyrosine, and valine.

5. The hair treatment formulation as recited in claim 1 wherein at least some of said composite nanoparticles comprise a predetermined amount of emollients and conditioners.

6. The hair treatment formulation as recited in claim 5 wherein said emollients and conditioners are selected from the group consisting of silicone oil, argan oil, wheat germ oil, soy bean oil, and olive oil.

7. The hair treatment formulation as recited in claim 1 wherein said intermediate layer comprises a plurality of thiolates.

8. The hair treatment formulation as recited in claim 1 wherein said outer layer comprises a predetermined amount of a chitosan.

9. The hair treatment formulation as recited in claim 8 wherein said chitosan is a non-modified chitosan.

10. The hair treatment formulation as recited in claim 8 wherein said chitosan is a modified chitosan.

11. A hair treatment formulation in solution, said hair treatment formulation comprising:
a plurality of composite nanoparticles suspended in an amount of said solution,
at least some of said plurality of composite nanoparticles having an inner core, an intermediate layer, and an outer layer, and wherein said intermediate layer comprises a predetermined amount of at least one thiolate
at least one treatment component being embedded in at least one of said inner core, said intermediate layer, or said outer layer, wherein said at least one treatment component is selected from the group consisting of cysteine, an emollient and a conditioner.

12. The hair treatment formulation as recited in claim 11 wherein said solution has a pH selected to effect opening of a plurality of hair cuticles upon application of said solution to a user's hair.

13. The hair treatment formulation as recited in claim 11 wherein said pH of said solution is about 9 or higher.

14. The hair treatment formulation as recited in claim 11 wherein said outer layer has an isoelectric point at a pH sufficient to effect opening of a plurality of hair cuticles upon application of said solution comprising said plurality of composite nanoparticles to a user's hair.

15. The hair treatment formulation as recited in claim 11 wherein said isoelectric point of said outer layer is greater than a pH of said solution.

16. The hair treatment formulation as recited in claim 15 wherein said isoelectric point of said outer layer is about 9.

17. The hair treatment formulation as recited in claim 11 wherein said intermediate layer has an isoelectric point at a pH sufficient to effect closing of a plurality of hair cuticles upon absorption of at least some of said plurality of composite nanoparticles into a corresponding plurality of hair cortex regions of a user's hair.

18. The hair treatment formulation as recited in claim 11 wherein said inner core has an isoelectric point at a pH sufficient to effect closing of a plurality of hair cuticles upon absorption of at least some of said plurality of composite nanoparticles into a corresponding plurality of hair cortex regions of a user's hair.

19. The hair treatment formulation as recited in claim 11 wherein said at least one treatment component is cysteine.

20. The hair treatment formulation as recited in claim 11 wherein said at least one treatment component is an emollient.

21. The hair treatment formulation as recited in claim 11 wherein said at least one treatment component is a conditioner.

* * * * *